(12) United States Patent
Ma et al.

(10) Patent No.: US 11,266,778 B2
(45) Date of Patent: Mar. 8, 2022

(54) PATENCY CHECKING SYSTEM

(71) Applicant: Becton, Dickinson and Company, Franklin Lakes, NJ (US)

(72) Inventors: Yiping Ma, Layton, UT (US); Joseph Spataro, Cottonwood Heights, UT (US); Huy Tran, Riverton, UT (US); Kathryn Willybiro, Park City, UT (US); Jonathan Karl Burkholz, Salt Lake City, UT (US); Bart D. Peterson, Farmington, UT (US)

(73) Assignee: ;Becton, Dickinson and Company, Franklin Lakes, NJ (US)

( * ) Notice: Subject to any disclaimer, the term of this patent is extended or adjusted under 35 U.S.C. 154(b) by 94 days.

(21) Appl. No.: 16/742,456

(22) Filed: Jan. 14, 2020

(65) Prior Publication Data

US 2020/0230315 A1    Jul. 23, 2020

Related U.S. Application Data

(60) Provisional application No. 62/794,434, filed on Jan. 18, 2019.

(51) Int. Cl.
| | | |
|---|---|---|
| *A61M 5/158* | (2006.01) | |
| *A61M 39/22* | (2006.01) | |
| *A61M 39/10* | (2006.01) | |

(52) U.S. Cl.
CPC ........ *A61M 5/158* (2013.01); *A61M 39/1011* (2013.01); *A61M 39/22* (2013.01); *A61M 2005/1588* (2013.01)

(58) Field of Classification Search
CPC ................ A61M 5/158; A61M 5/1452; A61M 2005/1403; A61M 39/1011; A61M 39/22; A61M 25/00; A61M 25/0097; A61M 2205/581; A61M 2205/582; A61M 2205/583; A61M 5/1454; A61B 5/150061; A61B 5/150053; A61B 5/153; A61B 5/15003; A61B 5/150007; A61B 5/15; A61B 5/1405; A61B 5/14
See application file for complete search history.

(56) References Cited

U.S. PATENT DOCUMENTS

| | | | |
|---|---|---|---|
| 5,439,452 A * | 8/1995 | McCarty | A61M 39/223 137/625.22 |
| 5,823,961 A | 10/1998 | Fields et al. | |
| 6,579,263 B1 | 6/2003 | Chernack | |
| 7,032,605 B1 * | 4/2006 | Dority | F16K 27/12 137/1 |
| 2002/0198496 A1 * | 12/2002 | Duchon | A61M 5/16827 604/154 |

(Continued)

FOREIGN PATENT DOCUMENTS

| | | |
|---|---|---|
| WO | 92/11891 | 7/1992 |
| WO | 2015/200620 | 12/2015 |

*Primary Examiner* — Bhisma Mehta
*Assistant Examiner* — Neeraja Gollamudi
(74) *Attorney, Agent, or Firm* — Kirton McConkie; Whitney Blair; Kevin Stinger (57) ABSTRACT

A patency checking system, may include a fluid path to be coupled to an intravenous (IV) device at a distal end of the fluid path; a patency port formed along a length of the fluid path; and a plunger fluidically coupled to the fluid path at the patency port to selectively draw blood into the fluid path to confirm patency of the fluid path.

19 Claims, 4 Drawing Sheets

(56) References Cited

U.S. PATENT DOCUMENTS

| | | | |
|---|---|---|---|
| 2009/0247985 A1* | 10/2009 | Melsheimer | A61J 1/2096 604/506 |
| 2009/0254049 A1* | 10/2009 | Adams | A61M 5/16881 604/247 |
| 2017/0106142 A1* | 4/2017 | Hochman | A61M 19/00 |

* cited by examiner

PATENCY CHECKING SYSTEM

RELATED APPLICATIONS

This application claims the benefit of United States Provisional Patent Application No. 62/794,434, filed on Jan. 18, 2019, and entitled PATENCY CHECKER, which is incorporated herein in its entirety.

BACKGROUND

Intravenous (IV) devices such as peripheral intravenous catheter (PIVC) may be introduced into a patient's blood vessels in order to provide a fluid path into the blood stream of the patient. For example, IV devices and associated therapy systems may be used for infusing fluids, such as a saline solution, various medicaments, and parenteral nutrition, into a patient. Intravenous therapy systems may also be used for withdrawing blood from the patient.

During use of these IV devices, a needle and/or catheter of the IV device may remain within the patient's blood vessel for any number of applications of the saline solution, various medicaments, and parenteral nutrition, into the patient's bloodstream. In some examples, the IV devices may remain within the blood vessels of the patient for up to 10 days. During this time within the patient's body, certain complications may occur relative to the IV device/patient body interface. One complication may include the patency of the IV throughout the use of the IV device. In the present specification and in the appended claims, the term "patency" is the state of an IV or other catheter devices of being unblocked and open to act as a fluidic path into a patient's body. During such long periods of time when the IV device is within the patient's body, the patency of the IV device may be compromised. In order to check patency, a clinician may couple a syringe to the IV device, draw out an amount of blood, or pass an amount of saline solution into the IV device. During the blood draw, the clinician may check to see if an amount of blood into a tube coupling the IV device to the syringe at a connection port on the IV device. During a saline solution infusion, the clinician may monitor for an appropriate flow of the saline solution into the patient's blood vessel and, where resistance is met, may determine that a complete lack of patency or a level of a lack of patency has occurred within the IV device. These saline solution infusion or blood draw processes may be completed periodically and/or prior to any infusion of saline solution, various medicaments, and parenteral nutrition, into the patient.

Because the IV device is to be maintained at a specific orientation at and within the patient's body, increased manipulation of the IV device may lead to certain IV device complications such as dislodgment, virus or bacteria introduction at the injection site, and, in some embodiment's phlebitis. Phlebitis is the inflammation of a blood vessel that, in some cases, may be a precursor ailment that may lead to relatively more serious medical conditions.

The subject matter claimed herein is not limited to embodiments that solve any disadvantages or that operate only in environments such as those described herein. Rather, this background is provided to describe an environment in which the presently described embodiments may operate.

SUMMARY

The present disclosure relates generally to a patency checking system. The patency checking system may include a fluid path to be coupled to an intravenous (IV) device at a distal end of the fluid path; a patency port formed along a length of the fluid path; and a plunger fluidically coupled to the fluid path at the patency port to selectively draw blood into the fluid path to confirm patency of the fluid path. The plunger may be, in some embodiments, be formed within a barrel to form a syringe. In an embodiment, the syringe may include a spring that biases the plunger in a non-draw state in order to prevent accidental blood draws when the patency checking system is not in use.

The patency checking system described herein, may also include a length of a tube as a fluid path to the IV device. The length may vary; however, the present specification contemplates that the length of the fluid path may exceed a distance away from the IV device such that the IV device is not directly manipulated by the clinician during a patency blood draw or patency saline solution infusion process.

The patency checking system described herein, may also include a valve formed along the fluid path and intermediate to the distal end of the fluid path and the plunger with a fluid flush reservoir fluidically coupled to the plunger such that the valve may be made to selectively allow for patency checking at an IV device and a drawing of fluid from the fluid flush reservoir to flush the IV device.

In some embodiments of the patency checking system, a linear motor or other motor device may be included to automatically draw the plunger within the syringe. The linear motor may be electrically coupled to a power source and an actuation button such that actuation of the button by the clinician causes the plunger to be drawn out to either cause an amount of blood to be drawn out of the IV device or saline solution out of the saline solution reservoir. In some embodiments, the patency checking system may include a force sensor to detect a force used to pull the plunger back. The force sensor further includes a notification module to present to a clinician a notification descriptive of when a detected force by the force sensor indicates that the force used to pull the plunger back indicates non-patency of the IV device.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

As used herein, the term "proximal" refers to a location on the needle of an intravenous therapy system that, during use, is closest to the clinician using the intravenous therapy system and farthest from the patient in connection with whom the device is used. Conversely, the term "distal" refers to a location on the needle of an intravenous therapy system that, during use, is farthest from the clinician using the intravenous therapy system and closest to the patient in connection with whom the intravenous therapy system is used.

As used herein, the term "top", "up" or "upwardly" refers to a location on the needle of this intravenous therapy system that, during use, is radially away from the longitudinal axis of the intravenous therapy system and away from the patient's skin. Conversely, as used herein, the term "bottom", "down" or "downwardly" refers to a location on the needle of this intravenous therapy system that, during use, is radially away from the longitudinal axis of the device and toward the patient's skin.

As used herein, the term "in" or "inwardly" refers to a location with respect to the needle of this intravenous therapy system that, during use, is toward the inside of the intravenous therapy system. Conversely, as used herein, the term "out" or "outwardly" refers to a location with respect to the needle of this intravenous therapy system that, during use, is toward the outside of the intravenous therapy system.

This invention is described herein using like reference numbers for like elements in the different embodiments. Although the embodiments described herein are used in connection for use as an intravenous therapy system to receive a blood sample or introduce a medicament into the body of a patient, it is to be understood that this intravenous therapy system is applicable to other medical devices where it is desirable for a needle and/or catheter to be inserted into a blood vessel of a patient. In addition, while the embodiments of the intravenous therapy system are satisfied by embodiments in many different forms, there are shown in the drawings and herein described in detail, preferred embodiments of the invention with the scope of the disclosure measured by the appended claims.

Figure 1:
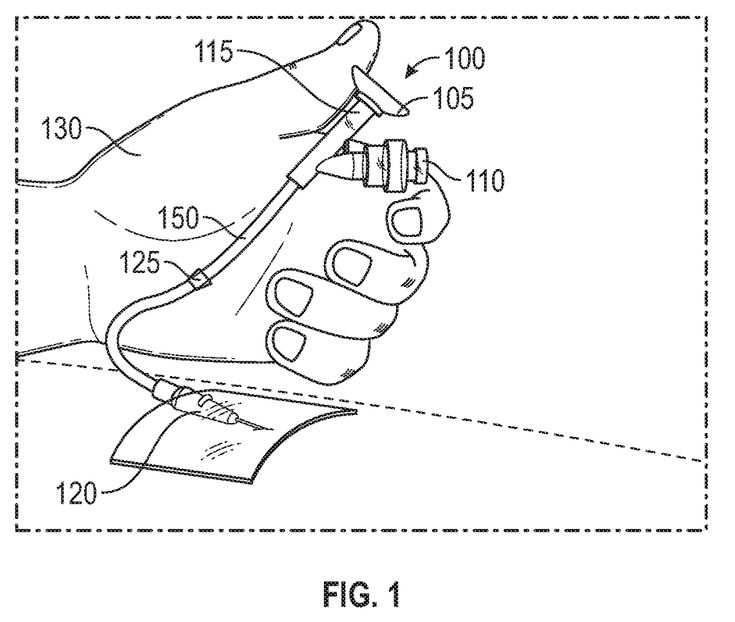
FIG. 1 is a perspective view of a patency checking system according to an embodiment of the present disclosure.

FIG. 1 is a perspective view of a patency checking system 100 according to an embodiment of the present disclosure. The patency checking system 100 may be communicatively coupled to an IV device 120 according to any embodiment described herein. The IV device 120 may be any device that may access a blood vessel within a patient and may include, among other elements, a needle and catheter to gain access the blood vessel. In an embodiment, the needle may be removed from the IV device 120 so that the catheter remains within the patient's blood vessel. In some embodiments, the catheter of the IV device 120 may remain within the patient's body for as long as 10 days. In order to prevent manipulation, the IV device 120 may be fluidically coupled to the patency checking system 100 that is placed off-site from the injection location of the IV device 120. Still further, because the patency checking system 100 is placed further off-site from the IV device 120, the IV device 120 may be secured to the patient using, for example, a tape thereby allowing access to the fluidic channels of the IV device 120 by the patency checking system 100 without a clinician manipulating the IV device 120 in the indwell state depicted in FIG. 1.

In an embodiment, the patency checking system 100 may include a plunger 105 housed within a barrel 115. In some embodiments, the barrel 115 and plunger 105 may form a syringe that is fluidically coupled to a fluid path 150 placed between the IV device 120 and patency checking system 100. In this embodiment, the syringe may access the fluid path 150 via a dedicated port used to couple the barrel 115 to the port formed in the fluid path 150. In the example embodiment shown in FIG. 1, the barrel 115 may form part of a port that is integrated into the fluid path 150 with the plunger 105 fluidically coupled to an interior of the fluid path 150.

The fluid path 150 may have a fluid path coupler 125. The fluid path coupler 125 may couple, in this embodiment, a fluid path 150 of the patency checking system 100 to a tube or other access port associated with the IV device 120. In an embodiment, the fluid path coupler 125 may include threading that interfaces with complementary threading coupler formed on the IV device 120. This fluid path coupler 125 that fluidically couples the patency checking system 100 to the IV device 120 may be maintained throughout the indwelling period of the IV device 120 so that the clinician operating the patency checking system 100 may not manipulate the IV device 120.

The patency checking system 100 may further include any number of fluidic ports 110. In the embodiment described herein, the fluidic port 110 may fluidically couple the patency checking system 100 to a fluid flush reservoir (not shown). In this embodiment, the fluid flush reservoir may provide a flushing fluid to the patency checking system 100 during operation of the patency checking system 100. In some embodiments, the fluidic port 110 may be used to introduce a saline solution, various medicaments, or parenteral nutrition, into a patient via the patency checking system 100 and IV device 120. Similar to the fluid path coupler 125, the fluidic port 110 may include threads or other types of coupling devices that allow the fluidic port 110 to be coupled to the fluid flush reservoir or other sources of the saline solution, various medicaments, and parenteral nutrition described herein.

Figure 2:
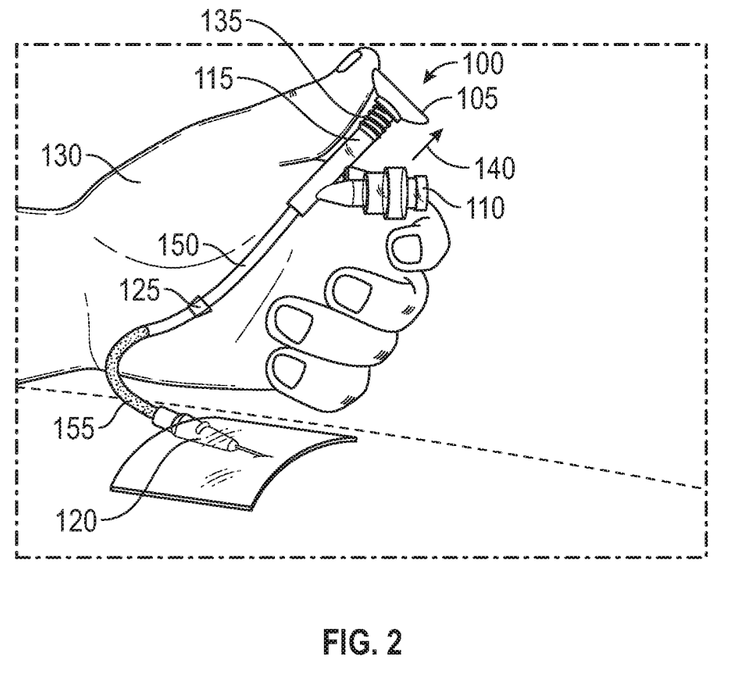
FIG. 2 is a perspective view of a patency checking system according to an embodiment of the present disclosure.

FIG. 2 is a perspective view of a patency checking system 100 according to an embodiment of the present disclosure. Similar to FIG. 1, the patency checking system 100 may be communicatively coupled to an IV device 120 according to any embodiment described herein. The IV device 120 may be any device that may access a blood vessel within a patient and may include, among other elements, a needle and catheter to gain access the blood vessel. In an embodiment, the needle may be removed from the IV device 120 so that the catheter remains within the patient's blood vessel. In some embodiments, the catheter of the IV device 120 may remain within the patient's body for as long as 10 days. In order to prevent manipulation, the IV device 120 may be fluidically coupled to the patency checking system 100 that is placed off-site from the injection location of the IV device 120. Still further, because the patency checking system 100 is placed further off-site from the IV device 120, the IV device 120 may be secured to the patient using, for example, a tape thereby allowing access to the fluidic channels of the IV device 120 by the patency checking system 100 without a clinician manipulating the IV device 120 in the indwell state.

In an embodiment, the patency checking system 100 may include a plunger 105 housed within a barrel 115. In some embodiments, the barrel 115 and plunger 105 may form a syringe that is fluidically coupled to a fluid path 150 placed between the IV device 120 and patency checking system 100. In this embodiment, the syringe may access the fluid path 150 via a dedicated port used to couple the barrel 115 to the port formed in the fluid path 150. In the example embodiment shown in FIG. 1, the barrel 115 may form part of a port that is integrated into the fluid path 150 with the plunger 105 fluidically coupled to an interior of the fluid path 150.

The patency checking system 100 may further include a spring 135 mechanically coupled to the plunger 105. FIG. 2 shows the plunger 105 being passed through and out of the barrel 115 by a clinician 130. The plunger 105 may be drawn out (arrow 140) of the barrel 115 a certain distance by the clinician 130 in order to, in an embodiment described herein, draw an amount of blood 155 from within the patient via the IV device 120. The blood 155 may be visually perceptible by the clinician 130 as the blood 155 is drawn through the tubing of the IV device 120 and/or the fluid path 150 of the patency checking system 100. The spring 135 may be biased such that it pulls the plunger 105 back into the barrel 115 when the clinician 130 releases the force applied to the barrel 115 during this patency checking process.

In an embodiment, the spring 135 may prevent the plunger 105 from being removed entirely from within the barrel 115. In similar or alternative embodiments, a stop may be formed between the plunger 105 and barrel 115 such that the plunger 105 may be prevented, mechanically, from being pulled entirely out of the barrel 115.

Again, the fluid path 150 may have a fluid path coupler 125. The fluid path coupler 125 may couple, in this embodiment, a fluid path 150 of the patency checking system 100 to a tube or other access port associated with the IV device 120. In an embodiment, the fluid path coupler 125 may include threading that interfaces with complementary threading coupler formed on the IV device 120. This fluid path coupler 125 that fluidically couples the patency checking system 100 to the IV device 120 may be maintained throughout the indwelling period of the IV device 120 so that the clinician operating the patency checking system 100 may not manipulate the IV device 120.

The patency checking system 100 may further include any number of fluidic ports 110. In the embodiment described herein, the fluidic port 110 may fluidically couple the patency checking system 100 to a fluid flush reservoir (not shown). In this embodiment, the fluid flush reservoir may provide a flushing fluid to the patency checking system 100 during operation of the patency checking system 100. In some embodiments, the fluidic port 110 may be used to introduce a saline solution, various medicaments, or parenteral nutrition, into a patient via the patency checking system 100 and IV device 120. Similar to the fluid path coupler 125, the fluidic port 110 may include threads or other types of coupling devices that allow the fluidic port 110 to be coupled to the fluid flush reservoir or other sources of the saline solution, various medicaments, and parenteral nutrition described herein.

Figure 3A:
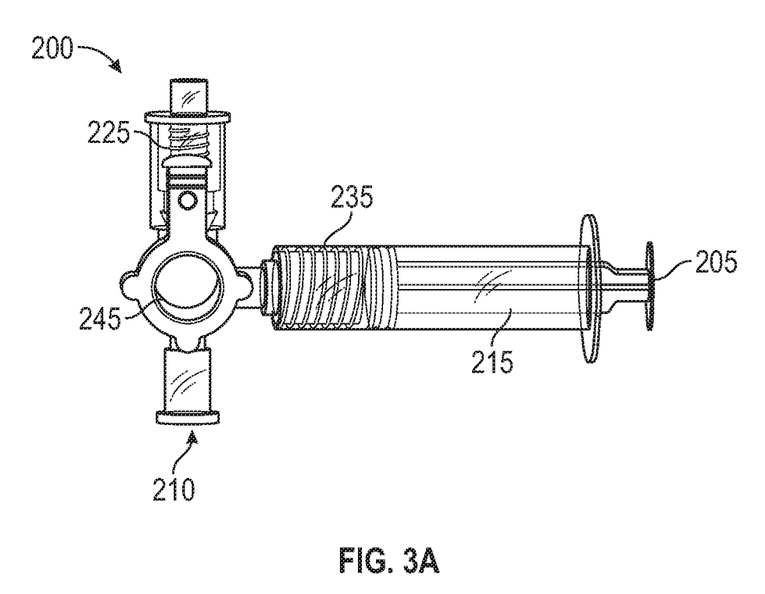
FIG. 3A is a top view of a patency checking system according to an embodiment of the present disclosure.

FIG. 3A is a top view of a patency checking system 200 according to an embodiment of the present disclosure. The patency checking system 200 may be communicatively coupled to an IV device (not shown) according to any embodiment described herein. The IV device may be any device that may access a blood vessel within a patient and may include, among other elements, a needle and catheter to gain access the blood vessel. In some embodiments, the catheter of the IV device may remain within the patient's body for as long as 10 days. In order to prevent manipulation, the IV device may be fluidically coupled to the patency checking system 200 that is placed off-site from the injection location of the IV device. Still further, because the patency checking system 200 is placed further off-site from the IV device, the IV device may be secured to the patient using, for example, a tape thereby allowing access to the fluidic channels of the IV device by the patency checking system 200 without a clinician manipulating the IV device in the indwell state.

The patency checking system 200 may further include a plunger 205 formed coaxially within a barrel 215 and fluidically coupled to the fluidic channels formed within the patency checking system 200. In an embodiment, the plunger 205 and barrel 215 may be in the form of a syringe as depicted in FIG. 3A. The barrel 215 may include, in some examples, threads that allow the barrel 215 with its plunger 205 to be fluidically coupled to the fluidic channels within the patency checking system 200.

The plunger 205 may include a plunger arm and a plunger head that may be used by a clinician to selectively pull the plunger 205 out of the barrel 215 and push the plunger 205 into the barrel 215. In an embodiment, the barrel 215 may include a spring 235 that mechanically couples the plunger 205 to an interior surface of the barrel 215. As described herein, the spring 235 may be biased such that it resists against movement of the plunger 205 out of the barrel 215. In an embodiment, the spring 235 may prevent the complete removal of the plunger 205 from the barrel 215. In an embodiment, the barrel 215 may include a formation formed in the barrel 215 that prevents the plunger 205 from being completely removed from the barrel 215.

The barrel 215 may also include any measurement indicators. These measurement indicators may indicate to a clinician the amount of gases removed from within a fluid path coupling the patency checking system 200 to an IV device.

The patency checking system 200 may further include a fluid path coupler 225. The fluid path coupler 225 may couple, in an embodiment, a fluid path (not shown) of the patency checking system 200 to a tube or other access port associated with the IV device. In an embodiment, the fluid path coupler 225 may include threading that interfaces with complementary threading coupler formed on the IV device. This fluid path coupler 225 that fluidically couples the patency checking system 200 to the IV device may be maintained throughout the indwelling period of the IV device so that the clinician operating the patency checking system 200 may not manipulate the IV device fluidically coupled thereto.

The patency checking system 200 may further include a fluidic port 210. In the embodiment described herein, the fluidic port 210 may fluidically couple the patency checking system 200 to a fluid flush reservoir (not shown). In this embodiment, the fluid flush reservoir may provide a flushing fluid to the patency checking system 200 during operation of the patency checking system 200. In some embodiments, the fluidic port 210 may be used to introduce a saline solution, various medicaments, or parenteral nutrition, into a patient via the patency checking system 200 and IV device. Similar to the fluid path coupler 225, the fluidic port 210 may include threads or other types of coupling devices that allow the fluidic port 210 to be fluidically coupled to the fluid flush reservoir or other sources of the saline solution, various medicaments, and parenteral nutrition described herein.

The patency checking system 200 may further include a valve 245. In an embodiment, the valve 245 may be formed between the barrel 215 and the fluid path coupler 225 that leads to an IV device. Additionally, in the example embodiment presented in FIG. 3A, the valve 245 may be placed between the barrel 215 and the fluidic port 210 that leads to a fluid flush reservoir or other medicament reservoirs. The valve 245 may be manually operated, in an embodiment, by a clinician in order to selectively draw blood through a fluidic path between the barrel 215 and the IV device via actuation of the plunger 205 in the barrel 215. This may be done while a fluidic passage between the barrel 215 and fluid flush reservoir is blocked or otherwise uncoupled by the valve 245. The valve 245 may also be manually operated, in an embodiment, by a clinician in order to selectively draw a flushing fluid from a fluid flush reservoir via actuation of the plunger 205 in the barrel 215.

FIG. 3A shows the valve 245 placed in an orientation such that the plunger 205 may be actuated to draw an amount of blood through the IV device as described herein. In this embodiment, the valve 245 may include a fluidic passage that fluidically couples an interior of the barrel 215 with a fluidic path within an IV device coupled to the patency checking system 200 via the fluid path coupler 225. FIG. 3A also shows the plunger 205 within the barrel 215 in a non-draw state. In this state, the plunger 205 is placed within the barrel 215 such that no gases are present within the barrel 215. During operation and with the valve 245 in the orientation shown in FIG. 3A, the clinician may engage in a blood draw procedure by pulling the plunger 205 as distance out of the barrel 215. This causes a negative pressure to form within the barrel 215 and fluidic path such that the negative pressure draws an amount of blood from within the patient's blood vessels and through the IV device fluidically coupled to the patency checking system 200 via the fluid path described herein. Because, in an embodiment, the fluid path comprises a tube that is translucent, the clinician may detect whether, upon actuation of the plunger 205. In an embodiment where the clinician detects blood being drawn out of the IV device, the clinician may conclude that the patency of the IV device is maintained. However, where, upon actuation of the plunger 205 by the clinician, no blood is drawn through the IV device and visibly detectable by the clinician at the fluid path, the clinician may conclude that the patency of the IV device is compromised with blood or other fluids blocking the fluidic paths formed within the IV device. At this point, the clinician may choose to remove the IV device and reinsert a new IV device that is free of blockages. In some embodiments, upon actuation of the plunger 205, the clinician may detect resistance at the plunger 205 above that expected but still visually detect blood being drawn from the IV device. In this embodiment, the clinician may determine that the IV catheter has partial patency such that fluid through the IV device may be slowed due to a non-complete blockage therein. At this point, the clinician may choose to change the IV device or conduct a fluid flushing process described herein.

During operation of the patency checking system 200, the valve 245 may be turned such that an arm of the valve 245 points towards the fluidic port 210. This may visually indicate to the clinician that a fluidic path is formed between the barrel 215 and a fluid flush reservoir coupled to the patency checking system 200 at the fluidic port 210. As described herein, the fluid flush reservoir may maintain an amount of flushing fluid used to flush an IV device fluidically coupled to the patency checking system 200 via the fluid path described herein. In this embodiment operation, the clinician may draw an amount of flushing fluid into the barrel 215 by actuating the plunger 205. While the clinician maintains the plunger 205 in this retracted state, the clinician may again turn the arm of the valve 245 towards the fluid path coupler 225 as shown in FIG. 3A. The clinician may then allow or cause the plunger 205 to pass further into the barrel 215 so as to evacuate an amount of flushing fluid out of the barrel 215, through the fluid path, and into the fluidic channels within the IV device. The flushing fluid may be passed through the fluidic channels of the IV device in an attempt to flush any blockages back into the blood vessels of the patient. In the embodiments presented herein, the flushing fluid may be a saline solution that includes purified water and a level of sodium chloride that matches or nearly matches the salinity of the patient's blood and, therefore, the inclusion into the patient's bloodstream may not adversely affect the health of the patient. The operation of the patency checking system 200 may continue with the clinician again engaging in a blood draw process as described herein in order to determine if the flushing fluid had sufficiently flushed any blockages within the IV device.

In an embodiment, the patency checking system 200 may include a locking device that allows a clinician to selectively lock the plunger 205 at a drawn, semi-drawn, and/or non-drawn state. By securing the plunger 205 at a non-drawn state, the clinician may prevent any accidental draw of blood or flushing fluid as described herein. By securing the plunger 205 in a drawn or semi-drawn state, the clinician may maintain an amount of flushing fluid or negative pressure while the clinician addresses the actuation of the valve 245 as described herein.

In an embodiment, the patency checking system 200 may include a linear motor (not shown) that is mechanically coupled to the plunger 205. The patency checking system 200 may further include a power source (not shown) to operate the linear motor. Still further, the patency checking system 200 may include an actuation button (not shown) that is electrically coupled to the power source and linear motor. During operation of this embodiment patency checking system 200, the clinician may actuate the actuation button so as to cause the linear motor to pull the plunger 205 from within the barrel 215 automatically. In this embodiment, the clinician may actuate the actuation button while viewing whether an amount of blood is being pulled from within the fluidic channels of the IV device or monitoring the flow of flushing fluid into the barrel 215.

In an embodiment, the patency checking system 200 may further include a force sensor (not shown) electrically coupled to the power source and a notification module (not shown) also coupled to the power source and force sensor. During operation, the force sensor may detect the force used to move the plunger 205 out of the barrel 215. In an embodiment where the force used to move the plunger 205 (either physically by the clinician or mechanically by the linear motor) does not exceed a certain threshold, the notification module may provide a visual indicator, audible indicator, haptic indicator, or no indicator at all indicating to the clinician that the force used to move the plunger 205 is sufficient to cause an amount of blood to be pulled out of the IV device. This indicates to a clinician that the fluidic channels within the IV device are patent allowing blood to pass therethrough. In an embodiment where the force used to move the plunger 205 (either physically by the clinician or mechanically by the linear motor) does exceed a certain threshold, the notification module may provide a visual indicator, audible indicator, haptic indicator, indicating to the clinician that the force used to move the plunger 205 is not sufficient to cause an amount of blood to be pulled out of the IV device. This indicates to a clinician that the fluidic channels within the IV device are not patent and that blood cannot be passed therethrough.

Figure 3B:
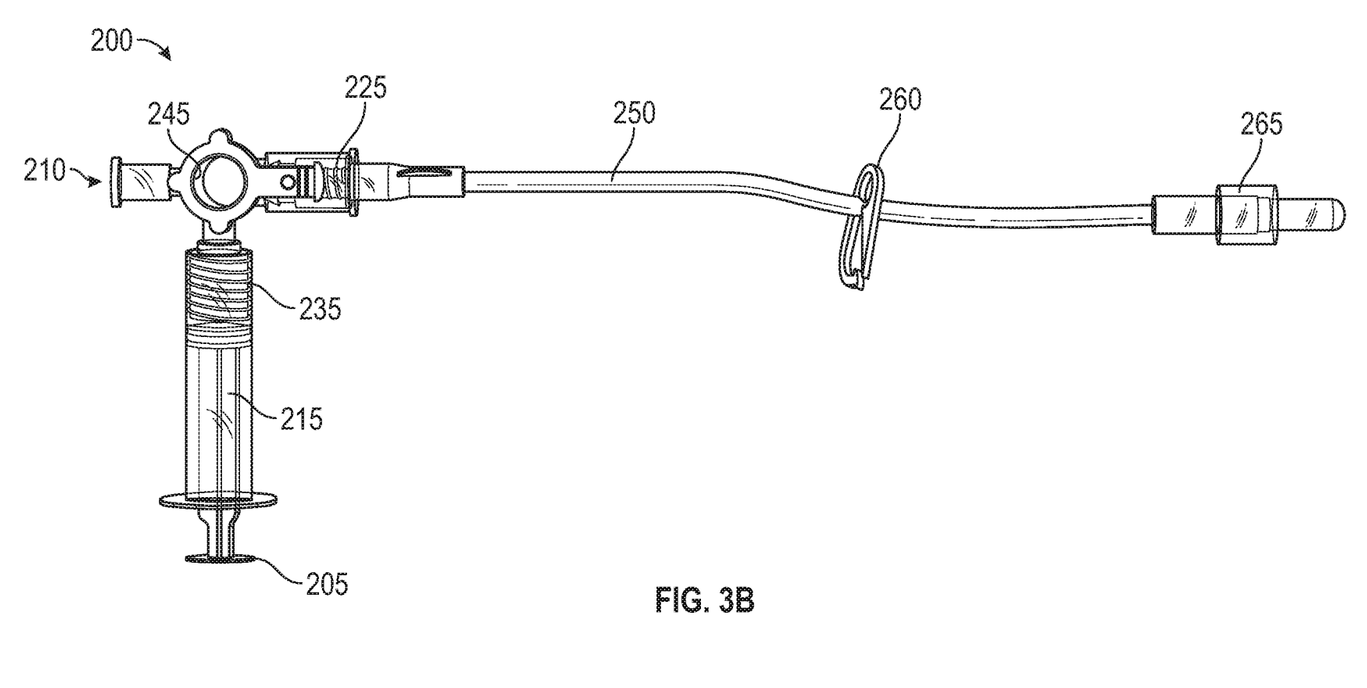
FIG. 3B is a top view of a patency checking system according to an embodiment of the present disclosure.

FIG. 3B is a top view of a patency checking system 200 according to an embodiment of the present disclosure. The patency checking system 200 may be communicatively coupled to an IV device (not shown) according to any embodiment described herein. The IV device may be any device that may access a blood vessel within a patient and may include, among other elements, a needle and catheter to gain access the blood vessel. In some embodiments, the catheter of the IV device may remain within the patient's body for as long as 10 days. In order to prevent manipulation, the IV device may be fluidically coupled to the patency checking system 200 that is placed off-site from the injection location of the IV device. Still further, because the patency checking system 200 is placed further off-site from the IV device, the IV device may be secured to the patient using, for example, a tape thereby allowing access to the fluidic channels of the IV device by the patency checking system 200 without a clinician manipulating the IV device in the indwell state.

The patency checking system 200 may further include a plunger 205 formed coaxially within a barrel 215, a spring 235 formed within the barrel 215, a fluid path coupler 225 and a fluidic port 210 similar to that described in connection with FIG. 3A. Although these elements described herein in connection with FIG. 3B may be similar to those described in connection with FIG. 3A, the present specification contemplates that the different embodiments of each of these elements may be reflected in the similar elements presented in FIG. 3B. Additionally, in some embodiments, the patency checking system 200 of FIG. 3B may also include the linear motor (not shown), power source (not shown), actuation button (not shown), force sensor (not shown), and notification module (not shown) that provide the functionalities as described in connection with FIG. 3A.

FIG. 3B further shows a fluid path 250 fluidically coupled to the patency checking system 200 via the fluid path coupler 225. The fluid path 250 may fluidically couple the patency checking system 200 to an IV device as described herein. In the embodiment shown in FIG. 3B, the fluid path 250 may be a translucent tube that allows a clinician to visually detect the passage of a fluid such as blood or a flushing fluid therein.

In an embodiment, an IV coupling device 265 may be formed at a distal end of the fluid path 250. As described herein, the IV coupling device 265 may mechanically couple the fluid path 250 to the IV device so that a fluidic channel may be formed from the patency checking system 200 to the IV catheter. The fluid path 250 may, in some embodiments, may have a length such that the patency checking system 200 is placed sufficiently off-site relative to the IV device so that the IV device is not accidentally manipulated. With the inclusion of the fluid path 250, the clinician may operate the patency checking system 200 as described herein without affecting the indwelling state of the IV device.

In an embodiment, the fluid path 250 may include a fluid path clamp 260. The fluid path clamp 260 may selectively prevent fluids such as gasses, blood, or flushing fluids from passing through the fluid path 250. In a specific embodiment, the fluid path clamp 260 may pinch off the fluid path 250 as the clinician is actuating the valve 245 and/or plunger 205 as described herein so as to prevent any accidental movement of the fluids as the valve 245 is turned.

Figure 3C:
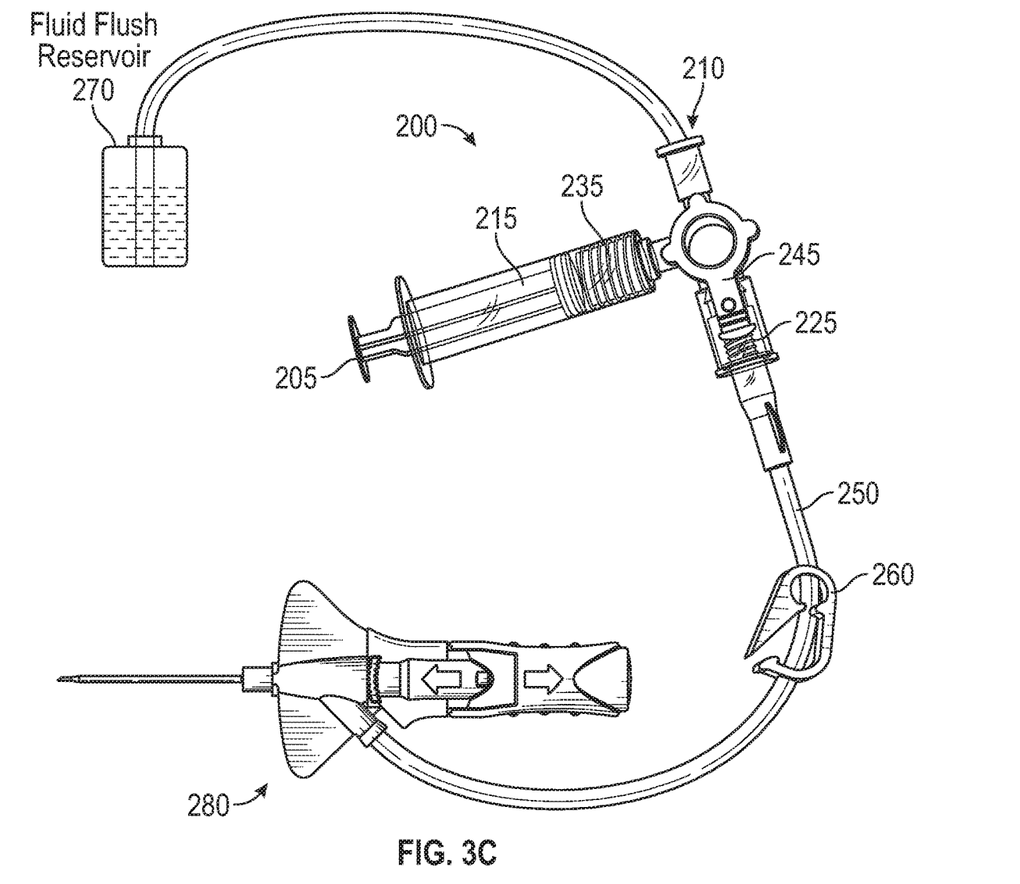
FIG. 3C is a top view of a patency checking system according to an embodiment of the present disclosure.

FIG. 3C is a top view of a patency checking system 200 according to an embodiment of the present disclosure. The patency checking system 200 may be communicatively coupled to an IV device 280 according to any embodiment described herein. The IV device 280 may be any device that may access a blood vessel within a patient and may include, among other elements, a needle and catheter to gain access the blood vessel. In some embodiments, the catheter of the IV device 280 may remain within the patient's body for as long as 10 days. In order to prevent manipulation, the IV device 280 may be fluidically coupled to the patency checking system 200 that is placed off-site from the injection location of the IV device 280. Still further, because the patency checking system 200 is placed further off-site from the IV device 280, the IV device 280 may be secured to the patient using, for example, a tape thereby allowing access to the fluidic channels of the IV device 280 by the patency checking system 200 without a clinician manipulating the IV device 280 in the indwell state.

The patency checking system 200 may further include a plunger 205 formed coaxially within a barrel 215, a spring 235 formed within the barrel 215, a fluid path coupler 225 and a fluidic port 210 similar to that described in connection with FIG. 3A. Although these elements described herein in connection with FIG. 3C may be similar to those described in connection with FIG. 3A, the present specification contemplates that the different embodiments of each of these elements may be reflected in the similar elements presented in FIG. 3C. Additionally, in some embodiments, the patency checking system 200 of FIG. 3C may also include the linear motor (not shown), power source (not shown), actuation button (not shown), force sensor (not shown), and notification module (not shown) that provide the functionalities as described in connection with FIG. 3A.

FIG. 3C further shows a fluid path 250 fluidically coupled to the patency checking system 200 via the fluid path coupler 225. The fluid path 250 may fluidically couple the patency checking system 200 to an IV device as described herein. In the embodiment shown in FIG. 3C, the fluid path 250 may be a translucent tube that allows a clinician to visually detect the passage of a fluid such as blood or a flushing fluid therein.

In an embodiment, the fluid path 250 may, form part of the IV device 280 that is mechanically and fluidically coupled to the patency checking system 200 at the fluid path coupler 225. The fluid path 250, in some embodiments, may have a length such that the patency checking system 200 is placed sufficiently off-site relative to the IV device 280 so that the IV device 280 is not accidentally manipulated. With the inclusion of the fluid path 250, the clinician may operate the patency checking system 200 as described herein without affecting the indwelling state of the IV device 280.

In an embodiment, the fluid path 250 may include a fluid path clamp 260. The fluid path clamp 260 may selectively prevent fluids such as gasses, blood, or flushing fluids from passing through the fluid path 250. In a specific embodiment, the fluid path clamp 260 may pinch off the fluid path 250 as the clinician is actuating the valve 245 and/or plunger 205 as described herein so as to prevent any accidental movement of the fluids as the valve 245 is turned.

FIG. 3C further shows a fluid flush reservoir 270 fluidically coupled to the fluidic port 210. In this embodiment, the fluid flush reservoir 270 may provide a flushing fluid to the patency checking system 200 during operation of the patency checking system 200. In some embodiments, the fluidic port 210 may be used to introduce a saline solution, various medicaments, or parenteral nutrition, into a patient via the patency checking system 200 and IV device 280. Similar to the fluid path coupler 225, the fluidic port 210 may include threads or other types of coupling devices that allow the fluidic port 210 to be coupled to the fluid flush reservoir 270 or other sources of the saline solution, various medicaments, and parenteral nutrition described herein. The fluid flush reservoir 270 may be used, during operation of the patency checking system 200, to draw an amount of flushing fluid therefrom in order to conduct an IV device 280 flushing process described herein.

Figure 4:
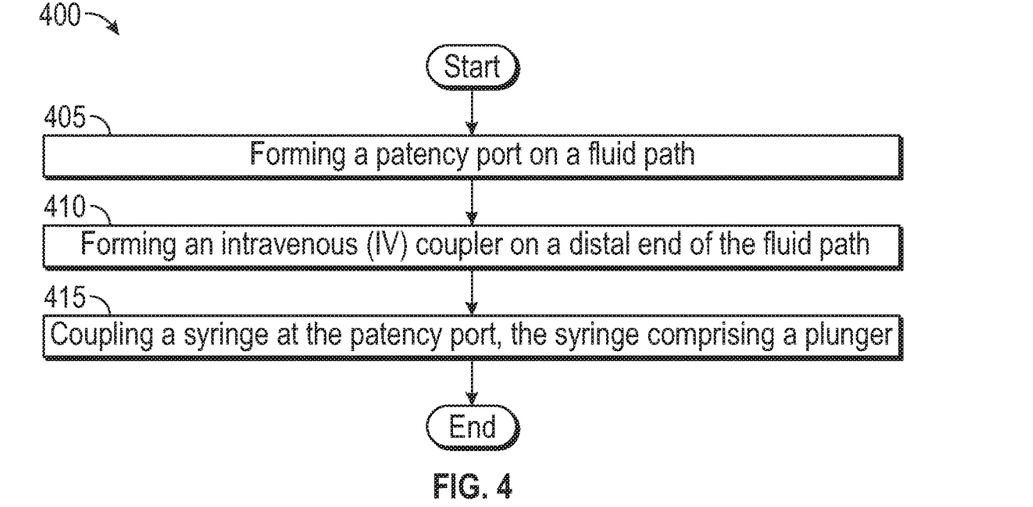
FIG. 4 is a flowchart depicting a method of manufacturing patency checking system according to some embodiments of the present disclosure.

FIG. 4 is a flowchart depicting a method 400 of manufacturing patency checking system according to some embodiments of the present disclosure. The method 400 may include, at block 405, forming a patency port on a fluid path. The patency port may be any location along a fluid path to which the barrel and plunger described herein may be coupled.

The method 400 may continue at block 410 with forming an intravenous (IV) coupler on distal end of the fluid path, the IV coupler may be any device that allows the patency checking system to be mechanically and fluidically coupled to the IV device as described herein.

The method 400 may further include coupling a syringe at the patency port, the syringe including a plunger. The syringe of the present method may the plunger and barrel described herein in connection with any of FIGS. 1-3C.

The method 40, in some embodiments, may further include adding those additional elements described in connection with FIGS. 1-3C. These additional elements include, but is not limited to, the linear motor, power source, actuation button, force sensor, notification module, fluid flush reservoir, and fluid path clamp, that provide the functionalities as described herein. The Again, it is understood that the embodiments of the present application may be combined. As an example, the embodiments of FIGS. 1-4 may be arranged to fit specific uses based on the type of action being conducted.

The presently described patency checking system may allow for the assessment of the patency of an IV device and the flushing of the IV device as described herein. The patency checking system allows for an IV device patency check without the need of connecting a syringe to the IV device during each of these checks. The patency checking system may be a stand-alone device, part of the catheter, or part of the extension set that places the patency checking system off site from the IV device so that the indwelling of the IV device may not be altered during the patency checking and fluid flushing processes described herein. This patency checking system reduces the chance of dislodgment of the IV device, infections at the injection site of the IV device, and the occurrence of phlebitis.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the disclosed embodiments.

The invention claimed is:

1. A patency checking system, comprising:
a fluid path comprising a distal end configured to be coupled to an intravenous (IV) device;
a patency port formed along a length of the fluid path and comprising a barrel;
a plunger fluidically coupled to the fluid path at the patency port and configured to be drawn proximally out of the barrel to draw blood from the IV device into the fluid path to confirm patency of the fluid path; and
a spring coupled to the plunger, wherein the spring is configured to pull the plunger distally into the barrel.

2. The patency checking system of claim 1, wherein the plunger is formed within the barrel to form a syringe that is fluidically coupled to the fluid path.

3. The patency checking system of claim 1, further comprising a valve formed along the fluid path and intermediate to the distal end of the fluid path and the plunger.

4. The patency checking system of claim 3, further comprising a fluid flush reservoir fluidically coupled to the plunger wherein the valve selectively allows for patency checking at the IV device and a drawing of fluid from the fluid flush reservoir to flush the IV device.

5. The patency checking system of claim 1, further comprising a locking device to lock the plunger in a non-drawn state.

6. The patency checking system of claim 1, further comprising a linear motor to automatically advance the plunger upon actuation of a button by a clinician.

7. The patency checking system of claim 6, wherein the linear motor advances the plunger a set distance based on a length of the fluid path.

8. The patency checking system of claim 1, further comprising a force sensor to detect a force used to pull the plunger back.

9. The patency checking system of claim 8, wherein the force sensor further comprises a notification module to present to a clinician a notification descriptive of when a detected force by the force sensor indicates that the force used to pull the plunger back indicates non-patency of the IV device.

10. A method of manufacturing a patency checking system, comprising:
forming a patency port on a fluid path, wherein the patency port comprises a barrel;
forming an intravenous (IV) coupler on a distal end of the fluid path and configured to couple to an IV device;
coupling a syringe at the patency port, the syringe comprising a plunger, wherein the plunger is configured to be drawn proximally out of the barrel to draw blood from the IV device into the fluid path to confirm patency of the fluid path; and
forming a spring coupled to the plunger, wherein the spring is configured to pull the plunger distally into the barrel.

11. The method of claim 10, wherein the spring is configured to bias the plunger to a non-drawn state.

12. The method of claim 11, further comprising fluidically coupling a fluid flush reservoir to the syringe to selectively allow for:
patency checking at the IV device coupled at the intravenous (IV) coupler and; and
drawing of fluid from the fluid flush reservoir to flush the IV device.

13. The method of claim 10, further comprising forming a valve intermediate to the patency port and the distal end of the fluid path.

14. The method of claim 10, further comprising forming a locking device on the syringe to lock the plunger in a non-drawn state.

15. The method of claim 10, further comprising mechanically coupling a linear motor and motor actuation button to the plunger to automatically advance the plunger upon actuation of the motor actuation button by a clinician.

16. A blood infusion system, comprising:
an intravenous (IV) device;
a fluid path comprising a distal end configured to be coupled to the intravenous (IV) device;
a patency port formed along a length of the fluid path and comprising a barrel;
a plunger fluidically coupled to the fluid path at the patency port and configured to be drawn proximally out of the barrel to draw blood from the IV device into the fluid path to confirm patency of the fluid path; and
a spring coupled to the plunger, wherein the spring is configured to pull the plunger distally into the barrel.

17. The blood infusion system of claim 16, wherein the spring is configured to pull the plunger distally into the barrel to a non-drawn state.

18. The blood infusion system of claim 16, further comprising:
a valve formed along the fluid path and intermediate to the distal end of the fluid path and the plunger; and
a fluid flush reservoir fluidically coupled to the plunger wherein the valve selectively allows for patency checking at the IV device and a drawing of fluid from the fluid flush reservoir to flush the IV device.

19. The blood infusion system of claim 16, further comprising a locking device to lock the plunger in a non-drawn state.

* * * * *